United States Patent [19]

Komatsuzaki et al.

[11] Patent Number: 5,298,015
[45] Date of Patent: Mar. 29, 1994

[54] WOUND DRESSING HAVING A POROUS STRUCTURE

[75] Inventors: Shigeru Komatsuzaki; Toshinobu Hirayama; Tetsuo Toyokawa, all of Yokohama, Japan

[73] Assignee: Nippon Zeon Co., Ltd., Tokyo, Japan

[21] Appl. No.: 854,765

[22] Filed: Mar. 20, 1992

Related U.S. Application Data

[63] Continuation of Ser. No. 545,734, Jun. 29, 1990, abandoned.

[30] Foreign Application Priority Data

Jul. 11, 1989 [JP] Japan .................................. 178833

[51] Int. Cl.$^5$ ........................ A61F 13/00; A61F 15/00
[52] U.S. Cl. ........................................ 602/46; 602/43; 604/369; 424/444; 424/445
[58] Field of Search ................... 604/304, 369; 623/15; 602/42, 43, 46; 424/444, 445, 447

[56] References Cited

U.S. PATENT DOCUMENTS

| | | | |
|---|---|---|---|
| 3,113,568 | 12/1963 | Robins | 128/156 |
| 3,800,792 | 4/1974 | McKnight et al. | 128/156 |
| 3,867,520 | 2/1975 | Mori et al. | 604/304 |
| 4,198,968 | 4/1980 | Kälberer et al. | 128/156 |
| 4,539,982 | 9/1985 | Bailly | 128/156 |
| 4,600,533 | 7/1986 | Chu | 128/156 |
| 4,625,720 | 12/1986 | Lock | 128/155 |
| 4,997,425 | 3/1991 | Shioya et al. | 128/156 |

OTHER PUBLICATIONS

Wise, Burn Wound Coverings, vol. II, pp. 1-9 and 53-61, 1984, U.S.A.

Primary Examiner—Paul Prebilic
Attorney, Agent, or Firm—Armstrong, Westerman, Hattori, McLeland & Naughton

[57] ABSTRACT

A dressing for a wound having a porous structure of continuous pores throughout the dressing made of minute filaments arranged in three dimensions and filmy links (viewed at a magnification of about 35 to 350) connecting the filaments. The porous structure has pores defined by the filmy interconnections. In other words, the wound dressing has a continuous open-celled structure in an expanded foam. The wound dressing can advantageously be made of a highly biocompatible material, such as poly-α-amino acid.

10 Claims, 13 Drawing Sheets

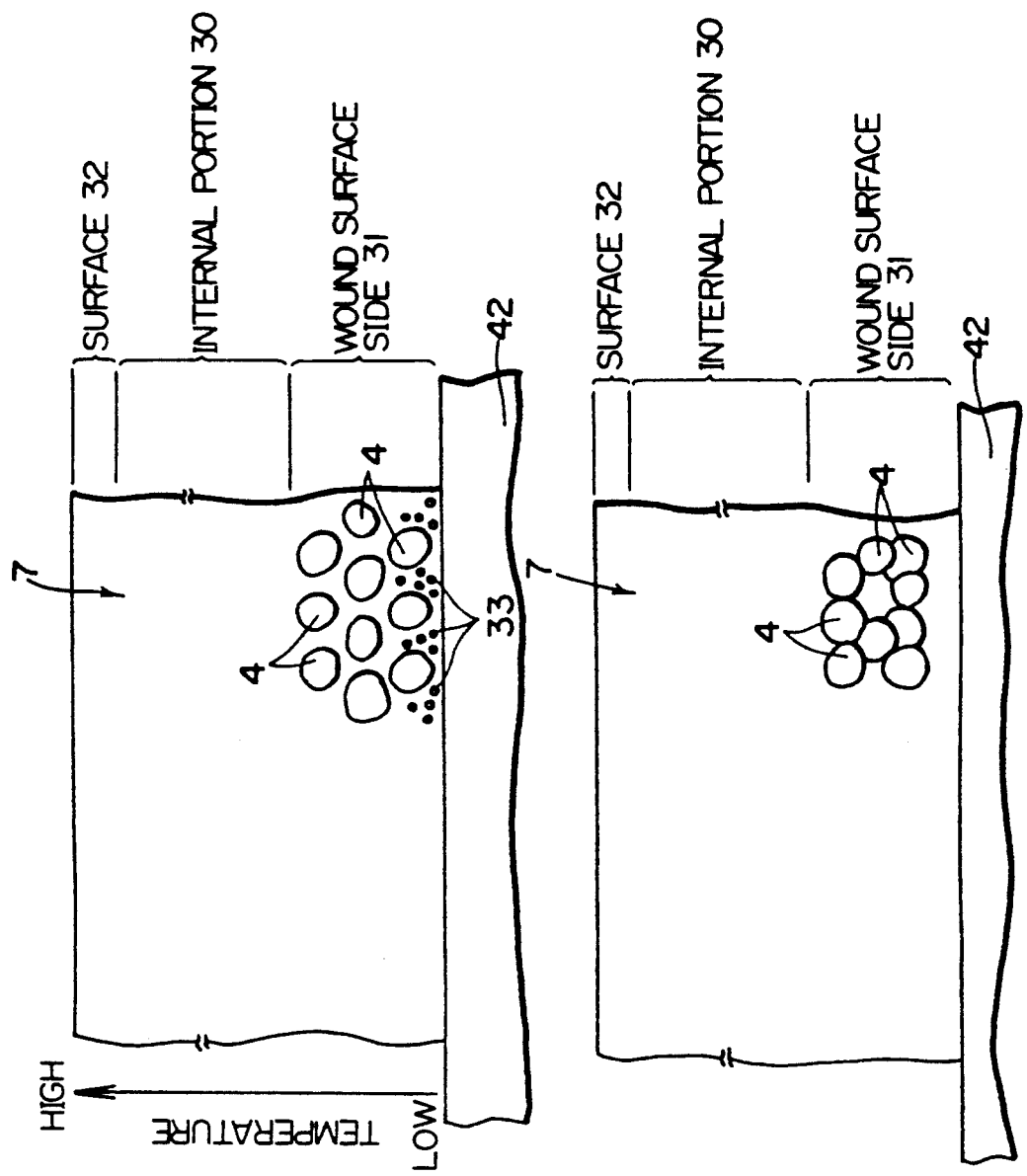

Fig. 8
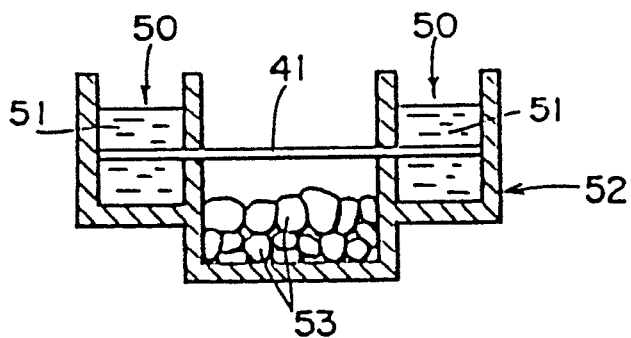
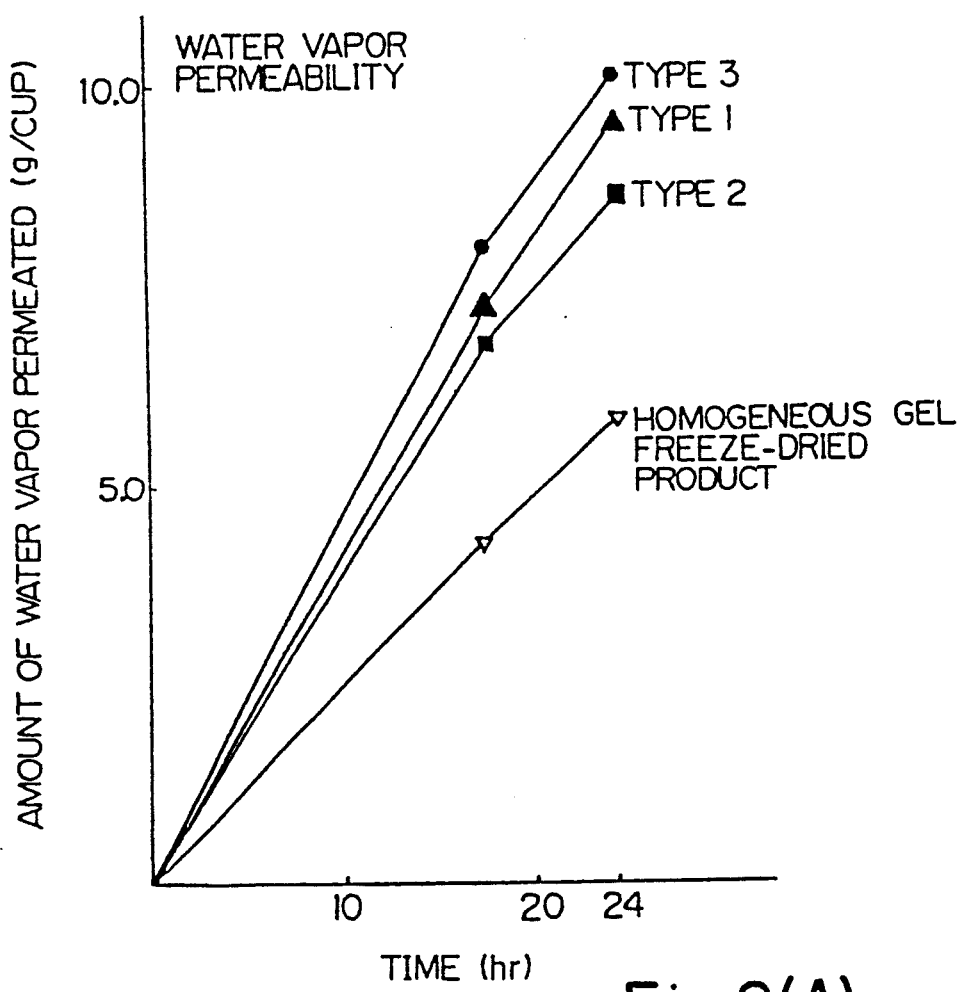
Fig. 8(A)

Fig. 9
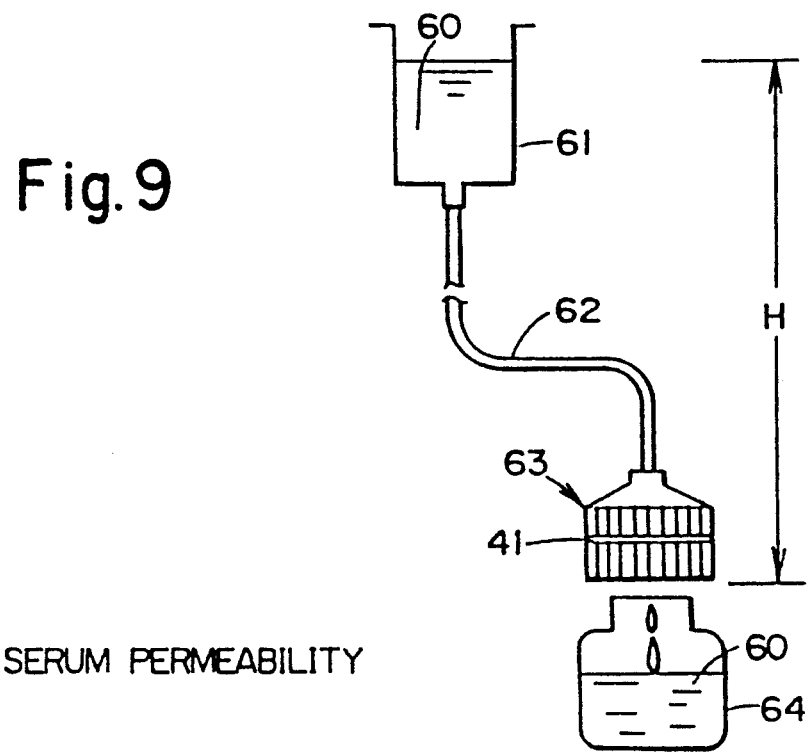
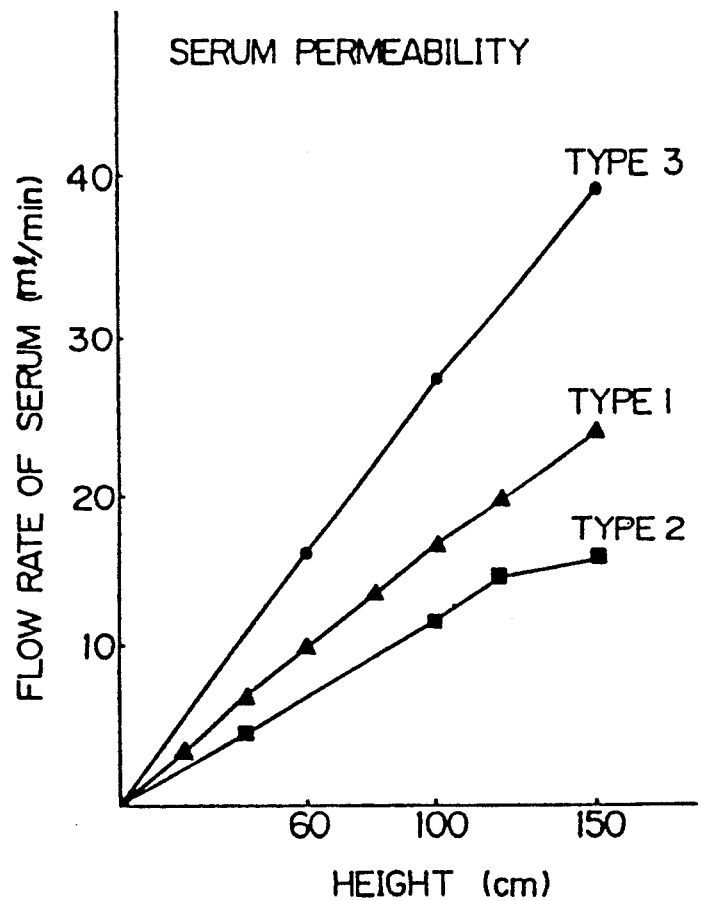
Fig. 9(A)

WOUND DRESSING HAVING A POROUS STRUCTURE

This application is a continuation of application Ser. No. 545,734 filed Jun. 29, 1990 now abandoned.

BACKGROUND OF THE INVENTION

1. Field of the Invention

The present invention relates to a wound dressing, and more particularly to a wound dressing which is suited for treatment of wounds, for example burns or trauma.

2. Description of the Prior Art

To date, various dressings have been developed to treat a broad range of skin defects due to burns, trauma or wounds.

While a variety of structural contrivances have been made for such wound dressings, those being often used at present are in the form that a silicone film is adhered to one side of a fabric or sponge structure to inhibit the invasion of bacteria This structure creates a primary vital adhesion by absorbing the exudate from the affected site to form fibrin, and in turn enables secondary vital adhesion by ensuring the subsequent penetration of fibroblasts and capillaries, thus resulting in the strong adhesion of the dressing to the wound surface. However, since the silicone film allows body fluid proteins to accumulate under the film, it has a great danger of becoming a source of nourishment for bacterial growth present on the wound surface, so that it has the shortcoming that the healing of wound is disturbed.

In the sponge structure as described above, moreover, its required performances such as good contacting ability with the above-mentioned exudate and blood, the efficiency of drug release, the good dressing ability of affected sites, etc. have been examined less sufficiently to date. For example, the structure disclosed in the U.S. Pat. No. 3,113,568 includes a barrier 20 which is made of foam having a network structure provided under a pad 11, as illustrated in FIGS. 12 and 13. Unit cells 21, which constitute this barrier 20, present a polyhedral structure having each face 22 (which is three-dimensionally linked by leg-like links 23 to become pores) formed. Therefore, this structure is simply network-like, not structurally satisfying each of the above-mentioned required performances to a sufficient extent. In other words, since the network-like structure is only linked by the leg-like links 23, it involves the following problems: the contact area having contact with exudate and blood is not sufficient; the mechanical strength of the network object is low; the drug dispersed from the network-like structure (which is contained in the structure beforehand) is released less efficiently; and the barrier effect on bacteria still remains to be improved. These problems are found generally in other known sponge structures.

OBJECTS AND SUMMARY OF THE INVENTION

Continuing various studies on wound dressings including the conventional therapeutic dressings for skin defects, the present inventor has succeeded in specifically modifying the porous structure of a sponge structure, thus reaching the present invention.

The first object of the present invention is to provide a wound dressing, which can enlarge the contact area between exudate or blood and the material, promote coagulation and incrustation, increase the mechanical strength, disperse the drug on the surface of the material to raise the efficiency of its release, enhance the barrier efficiency without reducing the permeability of moisture and vapor, and obtain a higher dressing effect at the state of incrustation.

The second object of the present invention is to provide a method by which the wound dressing can be manufactured reproducibly, both efficiently and well.

That is to say, the present invention relates to a wound dressing, wherein a porous structure having many pores is formed by a three-dimensional structure composed of a combination of minute filmy links, i.e., interconnections a magnification of about 35 to 350 in a wound dressing of the porous structure.

In addition, the method of manufacturing in accordance with the present invention is divided into the following three types:

The first manufacturing method is a method of manufacturing a wound dressing which has the following steps: warming with stirring a biocompatible or base material-containing solution to produce a homogeneous solution; cooling with stirring this homogeneous solution to create a dispersion gel in which the base material-containing gel particles are dispersed; and freeze-drying this dispersion gel.

The second manufacturing method is a method of manufacturing wound dressing which has the following steps: warming with stirring a base material-containing solution to produce a homogeneous solution; cooling with stirring this homogeneous solution to create a dispersion gel in which the base material-containing gel particles are dispersed; warming with stirring this dispersion gel; and freeze-drying this warm gel after it is allowed to cool.

The third manufacturing method is a method of manufacturing a wound dressing which has the following steps: warming with stirring a base material-containing solution to produce a homogeneous solution; cooling with stirring this homogeneous solution to create a dispersion gel in which the base material-containing gel particles are dispersed; and freeze-drying the dispersion gel under the presence of a liquid which inhibits the freezing of the dispersion gel which controls the freezing of this dispersion gel.

Other objects, features and advantages of the invention will appear more fully from the following detailed description thereof taken in connection with the accompanying drawings.

BRIEF DESCRIPTION OF THE DRAWINGS

FIGS. 1 to 11 illustrate the embodiments of the present invention, wherein:

FIG. 4 is a sectional perspective view of a wound dressing;

FIG. 5 is a sectional view showing a state of pouring dispersion gel into a mold;

FIG. 6 is a schematic view showing the freezing state of dispersion gel used for manufacturing a Type 1 wound dressing;

FIG. 7 is a schematic view showing the state of dispersion gel used for manufacturing a Type 2 wound dressing;

FIG. 8 is a sectional view showing a cup used for a vapor permeability test

FIG. 8A is a graph showing vapor permeability test results;

FIG. 9 is a sectional view showing a device used for a serum permeability test;

FIG. 9A is a graph showing serum permeability test results;

FIG. 10 is a graph showing the results of a plasma permeability test;

DESCRIPTION OF THE PREFERRED EMBODIMENTS

Figure 1A:
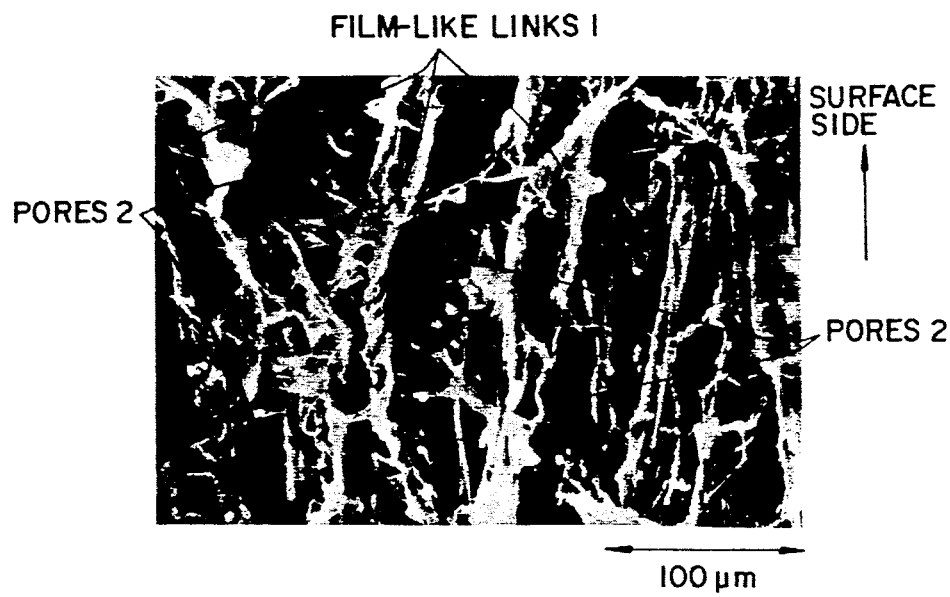
FIG. 1A is a scanning electron micrograph of a part of the film structure of the surface of a Type 1 wound dressing.

Wound dressings in accordance with the embodiments described below include, for example, the following three types (Type 1, Type 2 and Type 3):

Type 1

A type obtained by freeze-drying a polyamino acid dispersion gel.

Type 2

A type obtained by warming and then freeze-drying a polyamino acid dispersion gel.

Type 3

A type obtained by freeze-drying a polyamino acid dispersion gel containing cyclohexane.

While the manufacturing methods of these types will be described later, the structure of each type of wound dressing obtained is shown in FIGS. 1 to 3, respectively. In the description below, however, the respective regions of the surface, internal portion, and wound surface side of the wound dressing are as shown in the drawings. But usually, the surface represents a surface area having a depth of 10 to 200 μm from the outermost part, the wound surface side means an opposing surface area also having a depth of 10 to 200 μm from its outermost part, and the internal portion signifies a region between the surface and the wound surface side. FIG. 4 illustrates a section of a wound dressing in which a core or reinforcing material composed of nylon mesh 3 is embedded, causing the texture of the dressing to have changed with this core material as a border.

Figure 1B:
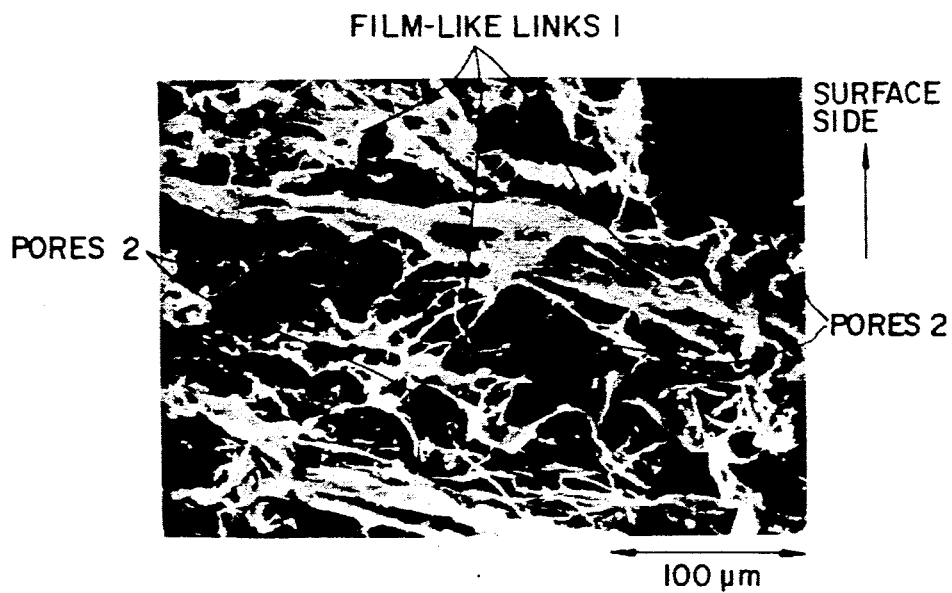
FIG. 1B is a similar scanning electron micrograph of the internal portion of the Type 1 wound dressing.
Figure 1C:
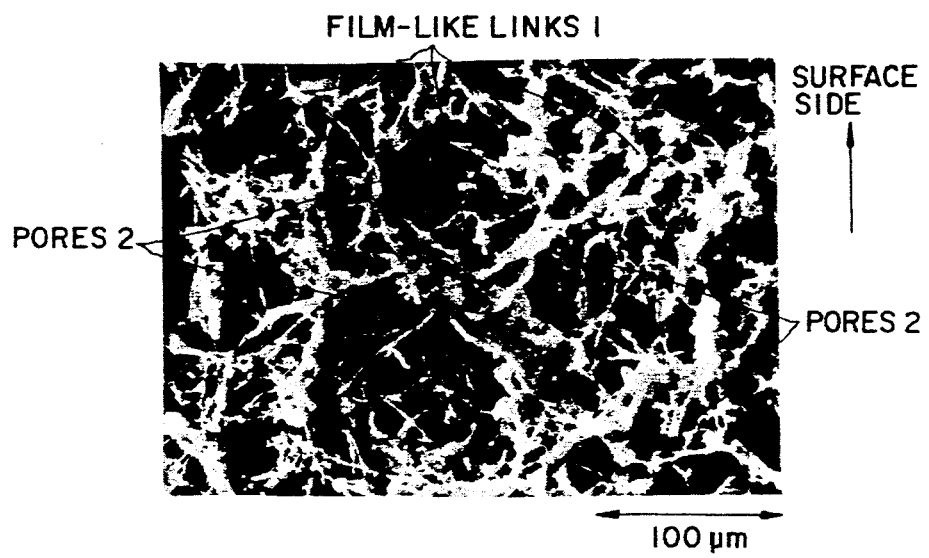
FIG. 1C is a similar scanning electron micrograph of the wound surface side of the Type 1 wound dressing.
Figure 1D:
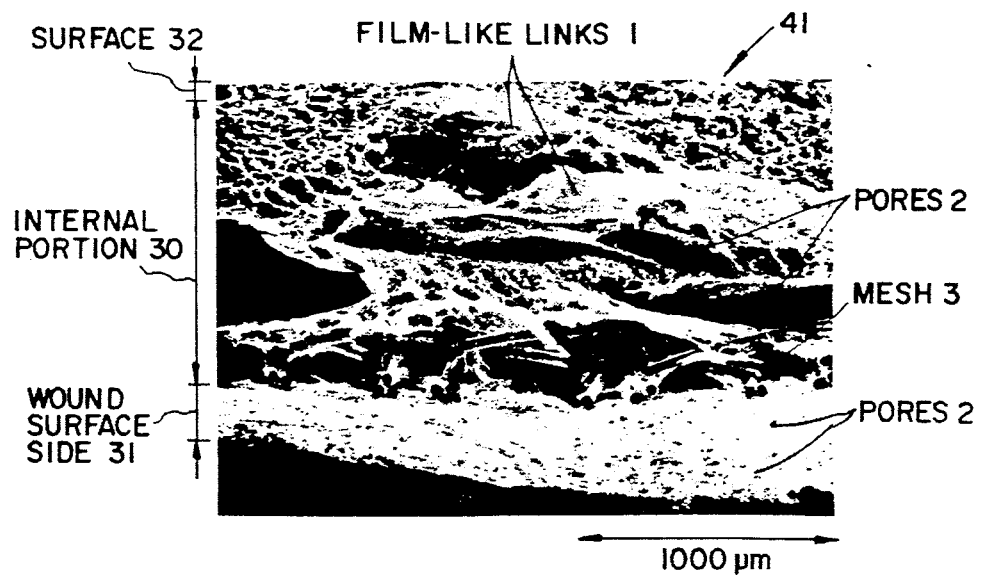
FIG. 1D is a scanning electron micrograph of the film structure of the cross section of the wound dressing.
Figure 13:
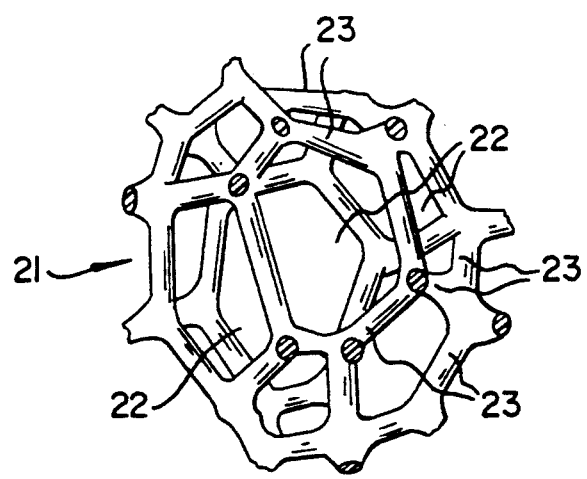
FIG. 13 is an enlarged perspective view of the network structural unit of a conventional wound dressing.

FIGS. 1A, 1B and 1C are the scanning electron micrographs of the film structure of a part each of the surface, internal portion and wound surface side of a Type 1 wound dressing. It can be seen from these micrographs that a Type 1 wound dressing has an unique porous structure which is so constituted as to contain pores 2 through three-dimensional linkage of minute film-like links (or film pieces). This is completely different from the porous structure which is constituted by leg-like links as shown in FIG. 13. To be specific, the film-like links 1 are produced in correspondence with dispersed particles in the dispersion gel as will be described later, possessing a relatively large width, and link between pores 2 in a continuous way (as continuous pores) without being isolated. The pores 2 themselves are large in size and numerous as well. Many of these pores are found especially in the internal portion of the wound dressing, but there are also numerous pores in the wound surface side, and a relatively tight surface layer is formed on the surface (see FIG. 1D showing a scanning electron micrograph of the film structure of the cross section.)

According to the Type 1 structure, the following marked effects, which have not been available to date, can be obtained.

(1) Since many pores 2 (which have a substantially uniform pore diameter in each region) are embedded in the three-dimensional structure formed by the film-like links 1, the contact area between exudate or blood from the wound surface and the material is enlarged so that coagulation and incrustation can be promoted, and mechanical strength can be increased.

(2) In addition, the release efficiency of a drug (which can be contained in the material beforehand, as will be described later) present in the dispersion on the surface of the biocompatible material can be increased.

(3) The barrier effect of the wound dressing can be raised without reducing its moisture and vapor permeability, and a more effective dressing can be obtained at the stage of incrustation.

Figure 2A:
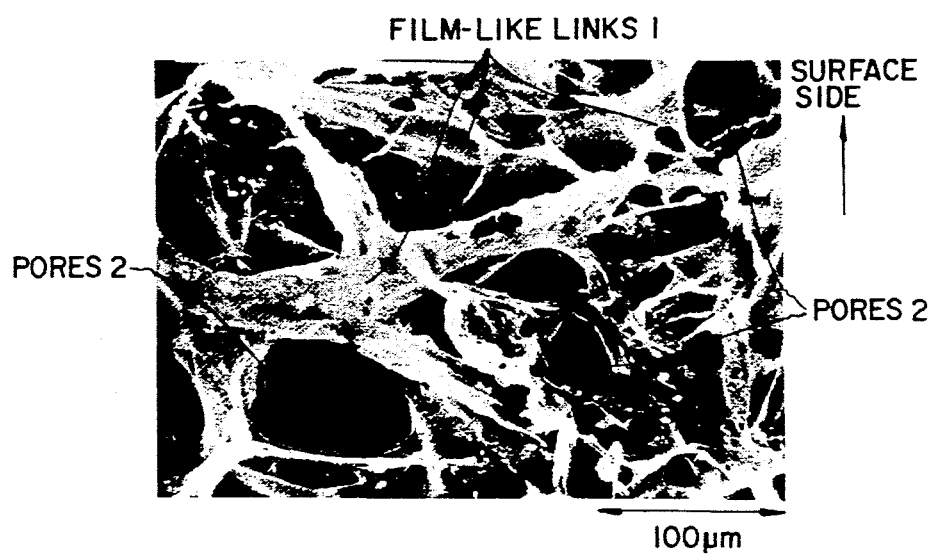
FIG. 2A is a scanning electron micrograph of the film structure of a part of the surface of a Type 2 wound dressing.
Figure 2B:
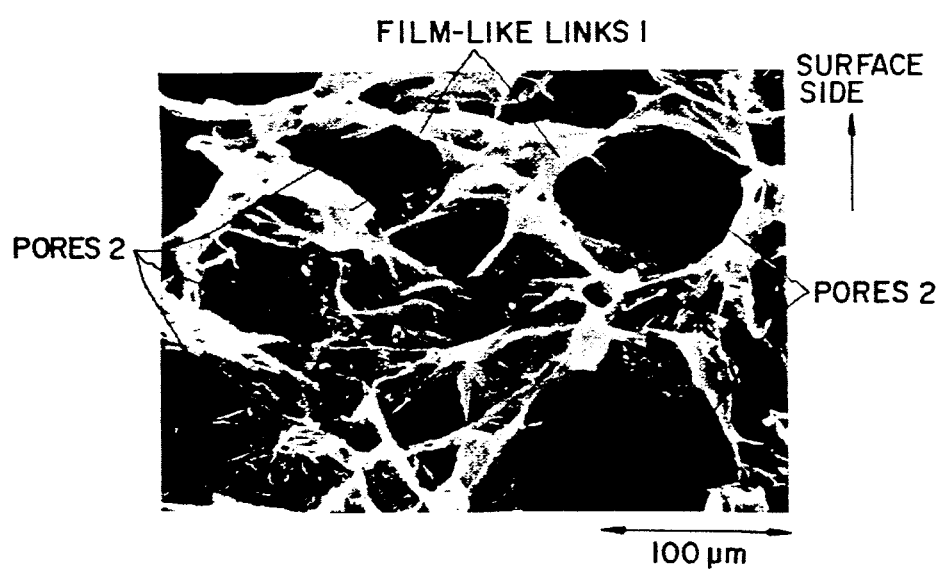
FIG. 2B is a similar scanning electron micrograph of the internal portion of the Type 2 wound dressing.
Figure 2C:
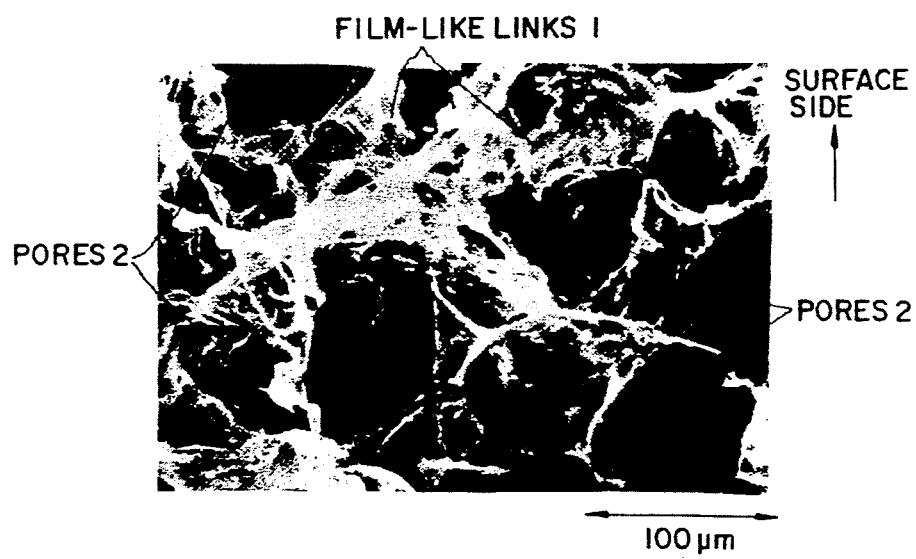
FIG. 2C is a similar scanning electron micrograph of the wound surface side of the Type 2 wound dressing.
Figure 2D:
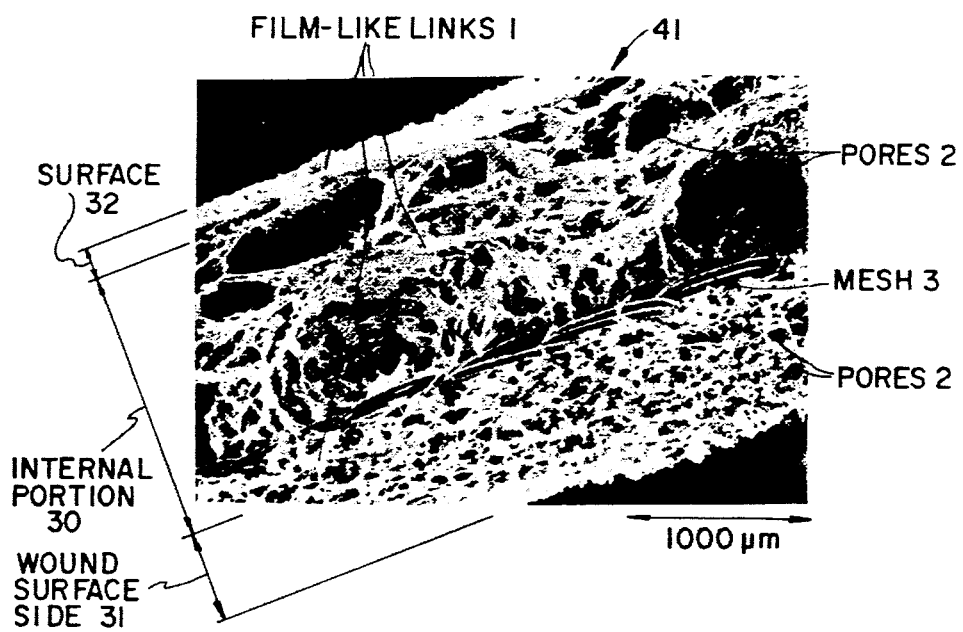
FIG. 2D is a scanning electron micrograph of the film structure of the cross section of the Type 2 dressing.

FIGS. 2A, 2B, and 2C are the scanning electron micrographs of the film structure of a part of each of the surface, internal portion and wound surface side of a Type 2 wound dressing, and FIG. 2D is a scanning electron micrograph of the cross section of the wound dressing. These micrographs reveal that a Type 2 wound dressing, like a Type 1, has an unique porous structure which is so constituted as to contain pores 2 through the three-dimensional linkage of minute film-like objects 1. And the structure of this Type 2 dressing is characterized by a greater width of the film-like links 1 and a larger diameter of pores 2, compared to a Type 1 dressing. This is thought to be due to the freeze-drying of the dispersion gel after warming, as shown in the manufacturing method which will be described later, which has already changed into an intermediate state of gel between dispersion and non-dispersion gel (i.e., a homogeneous gel consisting of a uniform phase with no dispersed particles) before freezing. A Type 2 dressing exhibits the properties as a Type 1 dressing, as well as having a better strength of the dressing than a Type 1.

Figure 3A:
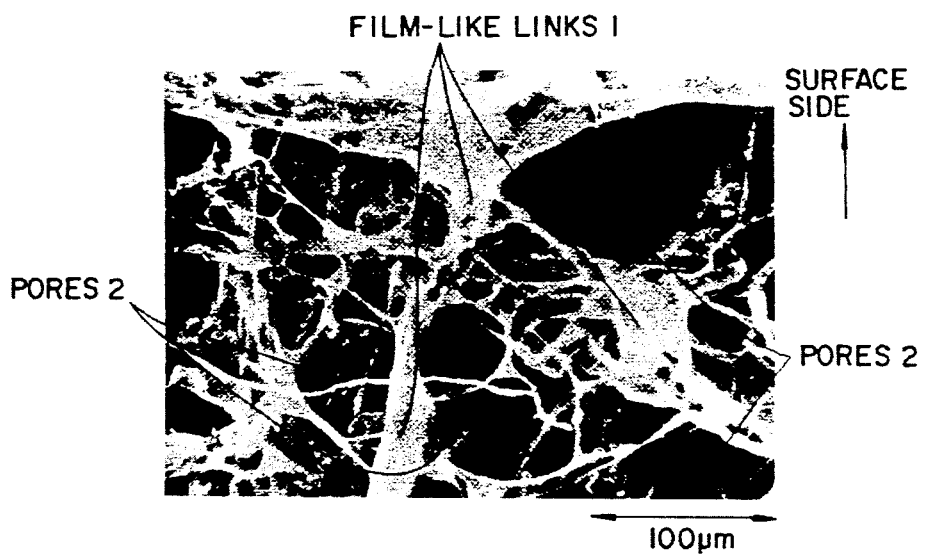
FIG. 3A is a similar scanning electron micrograph of the film structure of a part of the surface of a Type 3 wound dressing.
Figure 3B:
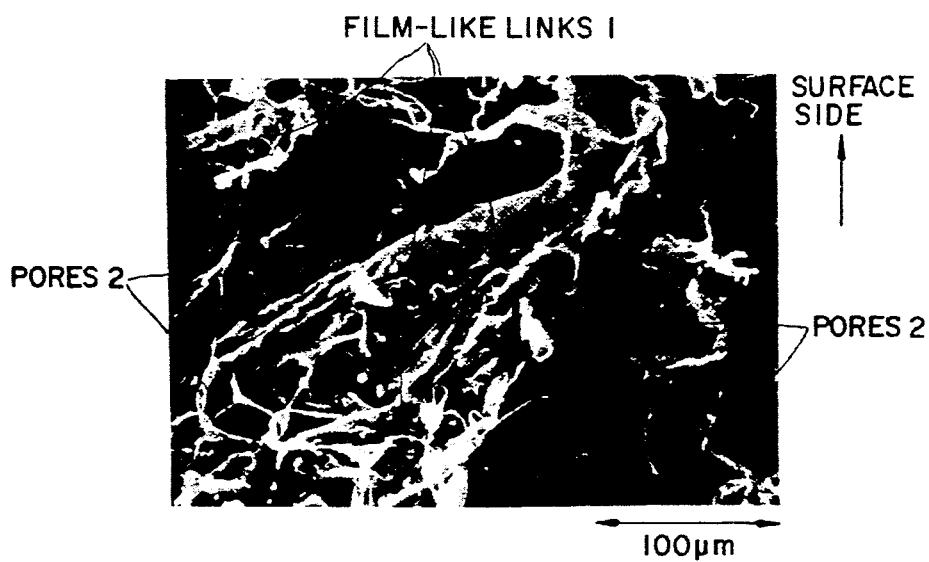
FIG. 3B is a similar scanning electron micrograph of the internal portion of the Type 3 dressing.
Figure 3C:
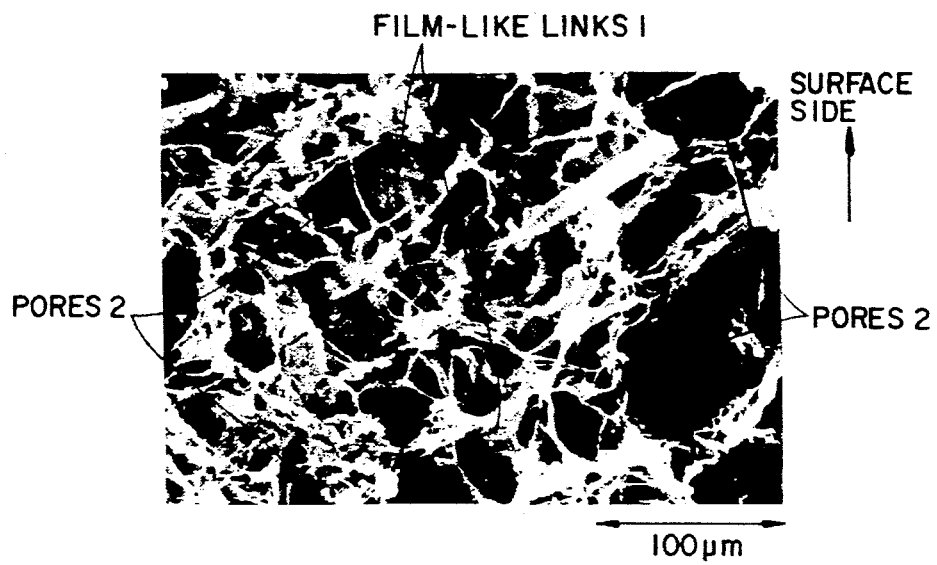
FIG. 3C is a similar scanning electron micrograph of the wound surface side of the Type 3 wound dressing.
Figure 3D:
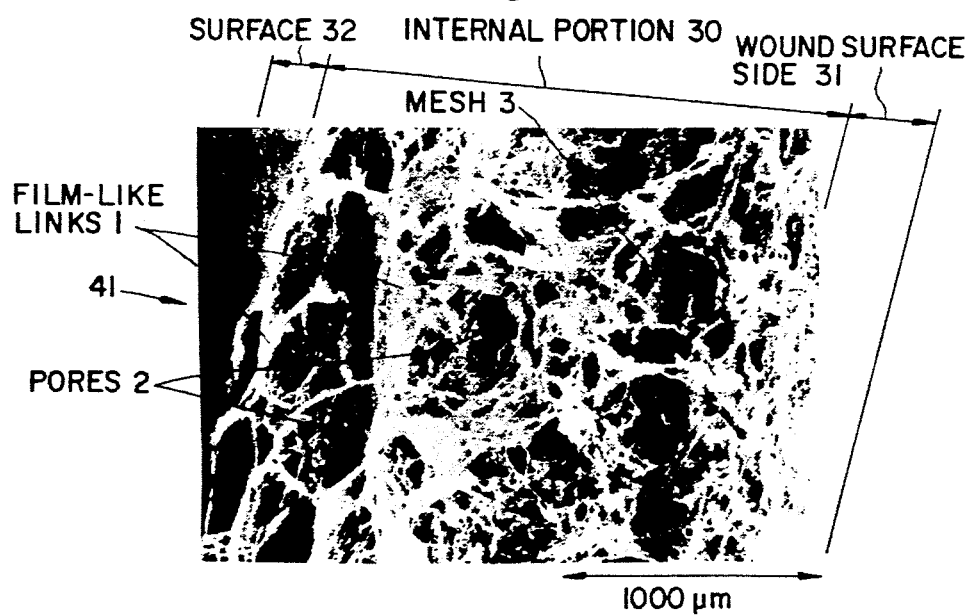
FIG. 3D is a scanning electron micrograph of the film structure of the cross section of the Type 3 wound dressings.
Figure 4:
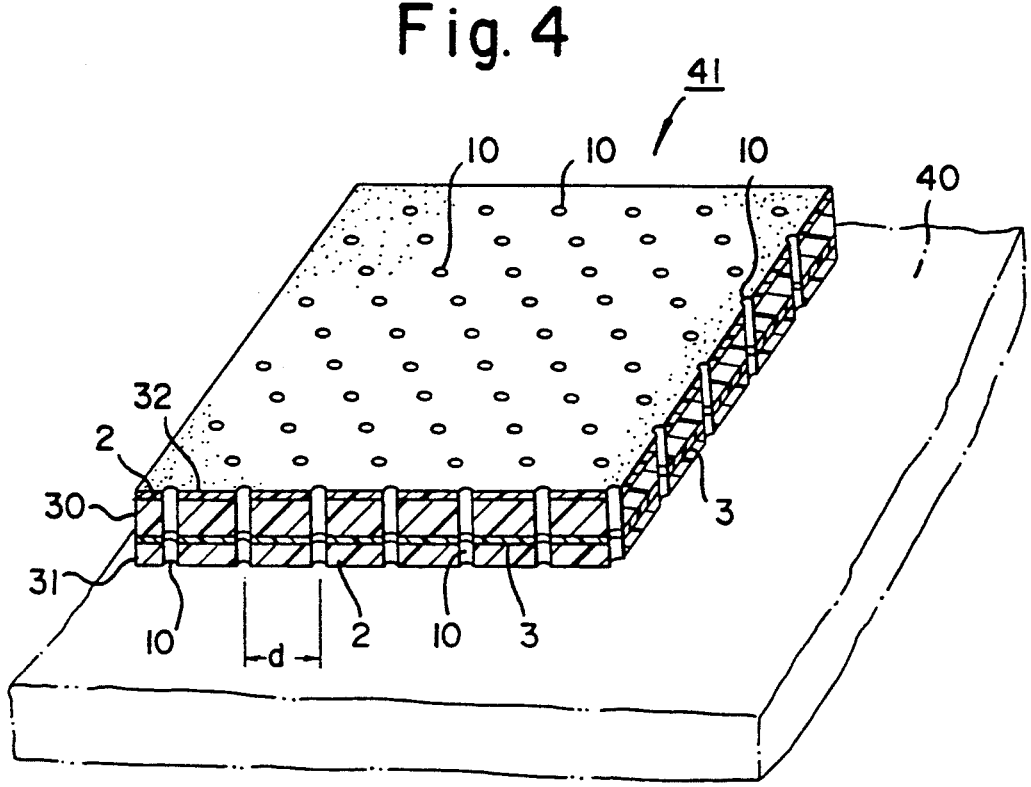

FIGS. 3A, 3B, and 3C show the scanning electron micrographs of the film structure of a part of each of the surface, internal portion and wound surface of a Type 3 wound dressing, and FIG. 3D shows a scanning electron micrograph of the film structure of the cross section of the wound dressing. These micrographs show that the Type 3 wound dressing, like Type 1, has a unique porous structure which is so constituted as to contain pores 2 through the three-dimensional linkage of minute film-like links 1. And it seems that in the structure of this Type 3 dressing, the film-like links 1 are linked in a more complicated fashion, compared to the Types 1 and 2 dressings. This is thought to be due to the presence of cyclohexane, as shown in the manufacturing method that will be described later, which has made it difficult for the dispersion gel to be frozen. The Type 3 dressing has the same properties as the Type 1 dressing, as well as the merits of both the Types 1 and 2, and is satisfactory not only in its moisture permeability and transudation but also in its strength.

Figure 5:
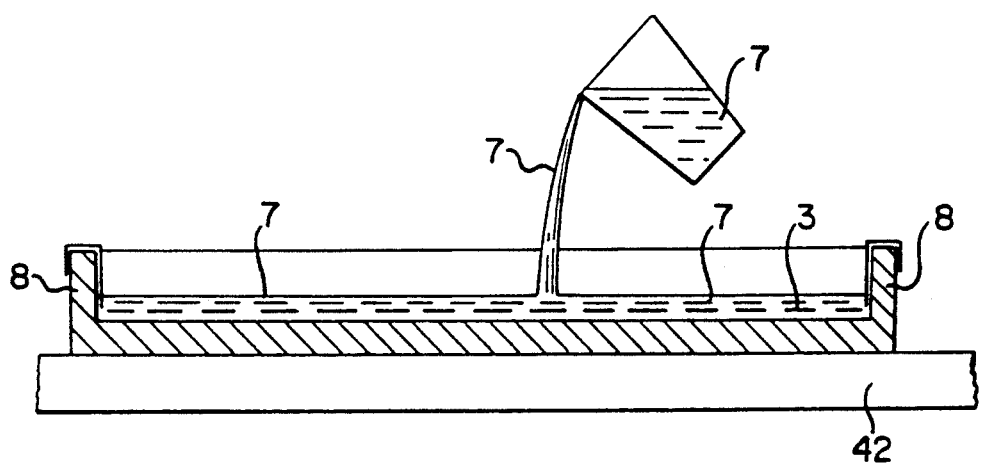

According to the dressings shown in FIGS. 1D, 2D, and 3D, respectively, nylon mesh 3 of a fibrous thickness ranging from 1 to 50 denier and a number of fibers per inch ranging from 1 to 100, is included. For example, mesh having a thickness of 15 denier and a division number of 40 per inch is embedded in the wound dressing. The biocompatible material is then entangled with this mesh, thus leading to improved strength. And it is seen that with the mesh 3 as a border, the film texture is relatively tight on wound surface 31, having large pores 2 on surface side 32 and small pores 2 on wound surface 31. When a dispersion gel 7 is poured into a mold 8 placed on a plate 42 as shown in FIG. 5, the mesh 3 serves as a filter to allow fine particles to pass through the mesh 3 to the wound surface side especially when the gel concentration is not lower than 0.2%, whereas coarse particles tend to remain closer to the surface side of the mesh 3 without passing through. As a result, as described above, the textures of both sides are varied with the mesh 3 as the border. Since the wound surface side has the pores 2 which are smaller, but more than the opposing surface of the mesh 3, its moisture permeability and strength, as well as drug release, are all satisfactory; and since the surface side of the mesh 3 has the pores 2 which are larger, its moisture permeability becomes still better, and its strength is also satisfactory due to the film-like links 1 having a large width and reinforcement effect added by the mesh 3, coupled with good pliability and cushiony properties. In addition, the texture of surface 32 is relatively tight, improving the effect of preventing the invasion of bacterial from outside. Such relative tightness of the surface 32 is estimated to be due to the following reason: as schematically illustrated in FIG. 6, a temperature gradient showing a gradual increase in temperature from the side of the plate 42 towards the surface is formed upon freezing, and crystallites 33 of a solvent (such as benzene) are produced between dispersed particles 4 from the side of the wound surface, so that the polyamino acid is pushed towards the surface, resulting in an increase in the density.

FIG. 4 is a sectional perspective view (in which a virtual line 40 represents a living body) of the wound dressing 41 in accordance with this embodiment.

This wound dressing 41 is a film-like object, the whole of which is composed of highly biocompatible or tissue-compatible porous poly-$\alpha$-amino acid and contains, for example, sulfadiazine silver as an antimicrobial agent. The dressing may have a thickness of 0.1 to 10 mm, for example, 1 mm, and a thin surface layer 32 having a thickness of 0.5 to 5 $\mu$m, especially 1 to 3 $\mu$m formed on the surface. The pore diameter of a pore 2 in the surface layer 32 may be 20 $\mu$m or less, and the pore diameter of a pore 2 in interior 30 may range from 20 to 500 $\mu$m. A reinforcing material composed of, for example, nylon mesh 3, embedded in the internal portion 30, increases the strength of the wound dressing 41 to prevent if from being torn during usage. This wound dressing 41 is also provided with many minute perforations 10 which pass through the dressing. The diameter of the minute perforations ranges from tens to several thousands $\mu$m, and their pitch d may be 10 mm.

Accordingly, body fluid discharged from the wound surface of the living body 40 passes through many pores 2 and infiltrates from the wound surface side 31 of the wound dressing 41 into the internal portion 30, as well as exudes by capillarity to the opposing surface layer 32 through the minute perforations 10. Thus, body fluid is effectively absorbed into the wound dressing 41 without remaining at the boundary between the wound surface of the living body 40 and the wound dressing 41. Accordingly, the danger of bacterial growth due to the retention of body fluid is prevented, leading to enhancement of the wound healing. The pores in the surface layer 32 are fine as described above, preventing bacterial invasion from the outside.

The antimicrobial agent in the wound dressing 41 can destroy bacteria on the wound surface and thereafter inhibit infections due to bacterial invasion from the outside. This requires the antimicrobial agent to be preferably released in trace amounts at a certain rate. In this case, the above-mentioned base material of the porous layer particularly is composed of hydrophobic poly-$\alpha$-amino acid, thereby markedly limiting the circulation of fluid in the layer and enabling the agent to be released over a prolonged period.

In this example, in addition, it is possible to allow the antimicrobial agent to be contained in the porous layer and develop its time-release effect. For this purpose, the content of the antimicrobial agent may be 0 to 100 parts by weight or 0 to 50 wt% (compared to 100 parts for the base polymer).

Highly biocompatible or tissue-compatible poly-$\alpha$-amino acids used in this example include poly ($\gamma$-benzyl-L-gultamate) (PBLG), poly(L-leucine), poly(N$^\epsilon$-carbobenzoxy-L-lysine), and the combinations of these amino acids. These poly-$\alpha$-amino acids are film materials having superb workability in particular since they are hydrophobic, readily polymerized, and soluble in benzene or dioxane, which can be removed by freeze-drying.

Moreover, local antimicrobial agents useable in this example include sulfadiazine silver, sulfadiazine zinc, sulfadiazine cerium, silver nitrate, and gentamicin. These antimicrobial agents are added to the above-mentioned highly histotropic porous film materials, and wound dressings can be produced with the resulting mixtures.

Furthermore, other agents such as vasoconstrictors (for hemostasis) and analgesics can be advantageously contained in the porous layer, in combined use with the above-mentioned antimicrobial agents.

In the wound dressing in accordance with this example, the core material 3 embedded in the porous layer (that is, lying in between) plays the role of giving mechanical strength to the dressing. Such a dressing can dress and protect the wound surface for a given treatment period as required, for example, for deep dermal burn and deep burn. The porous layer can then detach from the core material. Upon such detachment, the biocompatible base material remaining in the tissues reproduced is decomposed and absorbed in the living body. In this sense, particularly, unless the internal porous layer has some thickness (0.1 to 10 mm), as described above, the portion adhering to the body tissue would be detached. Further, the efficiency of removing the dressing after treatment can be improved by controlling the position at which the core material is embedded.

Applying the dressing to the wound surface leads to incrustation joined by exudate and blood. If the nylon mesh 3 is present in the dressing, the whole dressing can be removed by detaching the nylon mesh 3. This makes it necessary to properly control the position at which the nylon mesh should be incorporated.

The wound dressing in accordance with this example, when used with its attachment to the living body, preferably has sufficient flexibility to bend in correspondence with any movement of the living body. Otherwise, it would be readily detached from the living body if it has no flexibility. To provide the dressing with such flexibility, it is preferable that the above-mentioned core material 3 has proper flexibility (or elasticity). Such core materials 3 include natural fibers (such as protein fiber, cellulose fiber, and mineral fiber), synthetic fibers (made of, for example, polyurethane, polyolefin, polyvinyl chloride, polyvinylidene chloride, polyamide, silicone, and polyester) and metallic fibers (made of, for example, stainless steel and copper). The core material is desirably in the form of mesh, and can be produced in nylon mesh or silicone gauze.

It is desireable that a substance having good affinity for the living body (or enhancing the wound healing) is allowed to adhere to at least one side (especially the wound surface side) of the wound dressing in accordance with this example. A wound dressing laminated with a layer of such a substance can promote initial vital adherence and inhibit retention of the exudate between the dressing and the wound surface, thus accelerating the treatment. In the process of lamination, a porous layer of the above-mentioned substance is provided, and a dressing is then formed on this layer by the above-described method, or a solution of the substance is applied to the surface of the dressing, followed by freeze-drying. The above-mentioned substances include such serum proteins as fibrinogen, albumin, $\gamma$-globulin and fibronectin, collagens (including atherocollagen), gelatin, and mucopolysaccharides.

Among these, fibrinogen is a blood coagulating protein and forms fibrin by the action of thrombin. Since fibrin exhibits superb adhesion and proliferative properties towards fibroblasts, application of fibrinogen to the wound surface side of the dressing causes the development of its hemostatic effect and at the same time, reveals its good vital adhesion and therapeutic effect for the wound. In addition, since collagen is a material exhibiting excellent adhesive and proliferative properties towards fibroblasts, the dressing likewise exhibits vital adhesion and therapeutic effect for the wound.

Next, the process of manufacturing each type of wound dressing described above will be explained.

First, a mold 8 having the size of about 52 cm×14 cm, as shown in FIG. 5, is used, and nylon mesh 3 having a weight of about 0.26 g per cm$^2$ is extended at the level of 5 mm above the bottom surface of the mold. In preparing dispersion gel 7 (polyamino acid dispersion gel) to be poured into the mold 8, the following mixture is prepared to yield, for example, the concentration of poly(L-leucine) of 0.11 w/v%. The preparation is performed normally at a poly(L-leucine) concentration ranging from 0.01 to 1 w/v%.

| Benzene | 10 lit. (1 batch) |
|---|---|
| Poly(L-leucine) | 11 g |
| Sulfadiazine silver | 4 g |

While being stirred, this mixture is warmed to no less than 55° C., a temperature at which the solution undergoes no change in structure, especially to 70 to 75° C., with benzene not evaporated, and a uniform solution is obtained for over three hours. When converted to the volume of the above-mentioned mold 8, the composition of this homogeneous solution is as follows:

| Benzene | 728 ml (poured a 10 mm thickness) |
|---|---|
| Poly(L-leucine) | 0.8008 g |
| Sulfadiazine silver | 0.2912 g |

Benzene is preferred as the solvent, but another solvent of polyleucine can be used.

Production of Type 1

The homogeneous solution prepared above is cooled with stirring to a temperature range from no more than 55° C. to approximately room temperature, thereby leading to formation of the dispersion gel having dispersed particles with a particle size of 10 to 1000 $\mu$m containing poly(L-leucine), benzene, and sulfadiazine silver. Furthermore, after said homogeneous solution is cooled to room temperature as a homogeneous gel, the dispersion gel can be prepared by performing the operation of mashing or filtering the homogeneous gel. Nonetheless, it is more efficient to prepare the homogeneous solution by cooling it with stirring as described above. The dispersion gel obtained is composed of the gelled particles dispersed in a dispersion liquid (which is very slight in amount). Next, this dispersion gel is, as shown in FIG. 5, poured into the mold 8 at room temperature, and is then freeze-dried. The freezing temperature is set a 0 to −40° C. (e.g., −10° C.), and the subsequent drying is performed at 0 to 80° C. for example, 10° C. (the temperature of the plate 42) with the benzene being evaporated under reduced pressure. The state upon freezing is thought to be as follows: as schematically illustrated in FIG. 6, freezing progresses from the region near the plate 42 (wound surface); free benzene 33 between dispersed particles 4 is promptly crystallized; and the crystallization then occur gradually from the bottom towards the top, thus followed by the formation of a fibrous structure in the wound surface side 31, a network structure in the internal portion (internal layer) 30, and a relatively tight structure in the surface 32, respectively, during the above-mentioned course. The dispersion particles 4 correspond to the portion constituting the already described film-like matter 1, with many pores formed at the space where benzene has been evaporated.

Minute perforations 10 with 1 mm φ or 2 mm φ are formed in zigzags at intervals of 10 mm in porous film with the above-obtained nylon mesh built in, and a wound dressing of Type 1 is thus produced.

Production of Type 2

The dispersion gel prepared above is warmed with stirring at 56° C. for nor more than 10 minutes (e.g., 7.5 min.) or at 52° C. for 1 to 3 hours, thereby resulting in the preparation of gel in an intermediate state between the above-mentioned dispersion gel and homogeneous gel. This gel is, as shown in FIG. 5, poured into the mold with the stirring temperature maintained. It is then allowed to cool to form a soft gel.

This is freeze-dried in the same manner as described above, followed by the formation of minute perforations to produce a wound dressing of Type 2. In case of this Type 2 dressing, since the dispersion gel is warmed and poured into the mold as described above, it is thought that warming has allowed the interaction of the dispersed particles 4 prior to freezing as schematically illustrated in FIG. 7, causing the production of the gel in the intermediate state and thus resulting in the formation of a unique structure as shown in FIG. 2.

Production of Type 3

This type of wound dressing can be produced by the following two manufacturing methods, depending upon the time when cyclohexane is added:

(a) Added upon dissolution

When the above-described homogeneous solution is prepared, cyclohexane is added in an amount of 0.1 to 20%, preferably 0.5 to 10%, for example 1%, compared to the benzene, and is stirred at 70 to 75° C. for about one hour; then, it is cooled with stirring to a range from 55° C. to approximately room temperature, thus resulting in preparation of the dispersion gel. This dispersion gel is poured into the mold at room temperature in the same manner as described above and, after freeze-drying, a wound dressing of Type 3 is produced with minute perforations formed.

(b) Added after dispersion

Cyclohexane is added to the dispersion gel used for Type 1 in an amount of 0.1 to 20%, preferably 0.5 to 10%, for example, 1%, compared to the benzene, and this dispersion gel is poured into the mold at room temperature in the same manner as described above and, after freeze-drying, a wound dressing Type 3 is produced with minute perforations formed.

Since both wound dressings of (a) and (b) above are freeze-dried with the cyclohexane present (or is added) the cyclohexane makes it difficult for the gel as a whole to be frozen and brings it into an supercooled state. Thus, it is thought that this makes the process of freezing different from those of Type 1 and Type 2 and thus leads to the creation of a unique structure as shown in FIG. 3. Nonetheless, the cyclohexane is evaporated upon drying and does not remain in the flim.

Cyclohexane is believed to control the freezing process in this manner, but substances other than cyclohexane having no great differences in melting and boiling points from benzene can be used as an additive substance which exhibits the same effects as cyclohexane: for example, dioxane and cyclooctane. As for the amount of addition, 0.1 to 20% compared to the benzene, is appropriate, for example, 1 to 2% is desirable. If the amount is too low, then there is no additive effect, and if it is too high, the film structure obtained becomes defective.

The following tests were performed with each of the wound dressings as produced above.

(1) Tensile strength

The measurements of tensile strength along the extension of nylon mesh are as follows:

Type 1: 0.69 kg/cm$^2$
Type 2: 1.02 kg/cm$^2$

Both types exhibited a strength of 0.5 kg/cm$^2$ or more, proving that they were satisfactory in terms of strength.

(2) Vapor permeability

Using a cup 52, as shown in FIG. 8, a wound dressing 41 (the vapor permeating portion of which is a circle with a diameter of 6 cm) is extended, and with a ring-shape portion 50 tightened and sealed by paraffin 51. Water passing through the wound dressing 41 as permeating moisture was determined from an increase in the weight of a drying agent 53 under the atmosphere of 40° C. and 75% RH. The results are presented in FIG. 8.

It can be seen from these results that each of Type 1, 2, and 3 wound dressings have high moisture permeability. The uniform gel freeze-dried product shown in FIG. 8 represents a wound dressing made by freeze-drying the above-mentioned uniform gel as it was.

(3) Serum permeability

A millipore filter holder 63, which places a wound dressing 41 at the lower end of a pipe 62 to convey equine serum 60 from a transfusion bottle 61 containing the equine serum, was provided as shown in FIG. 9, and the flow rate of the serum dropping into a collection bottle 64 was measured while changing the height H. The results are illustrated in FIG. 9.

These results reveal that the serum permeability of Type 1, 2, and 3 wound dressings (especially Type 3) is satisfactory.

(4) Plasma permeability

Figure 10:
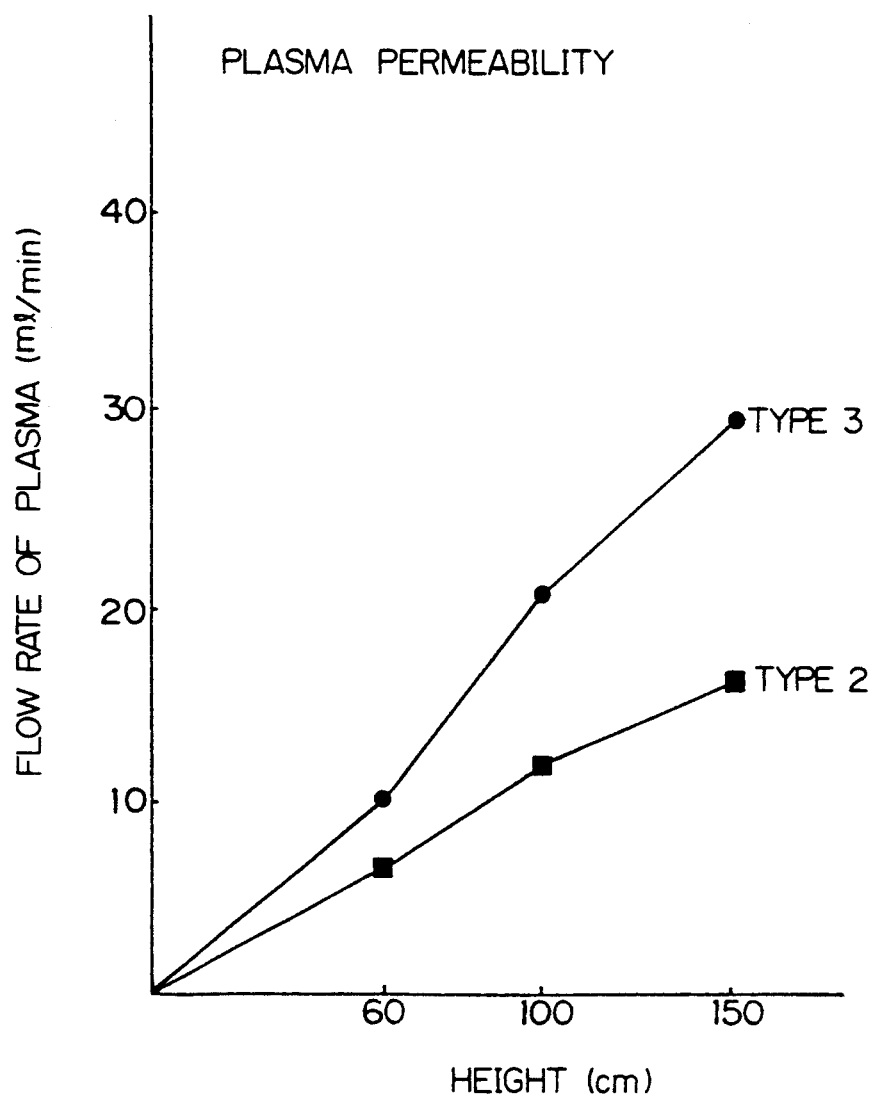
Figure 11A:
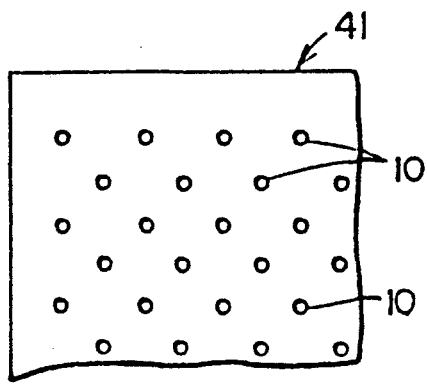
FIGS. 11(A) to 11(E) are respective plane views of a part of a wound dressing having various perforations.
Figure 11B:
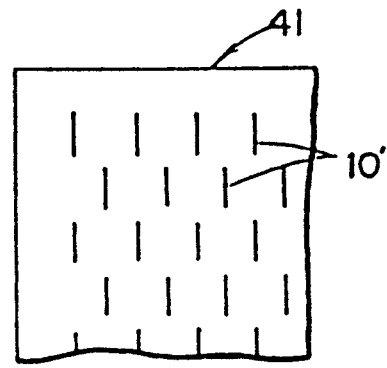
Figure 11C:
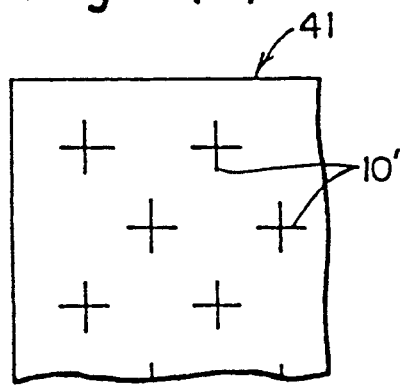
Figure 11D:
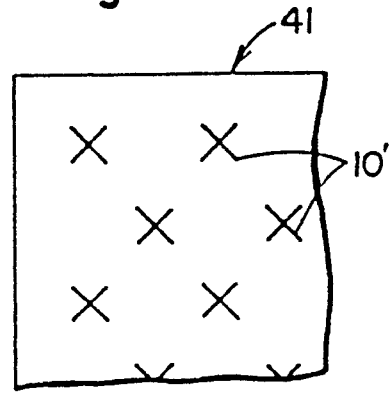
Figure 11E:
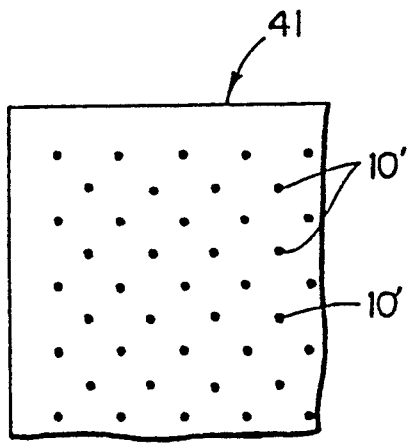
Figure 12:
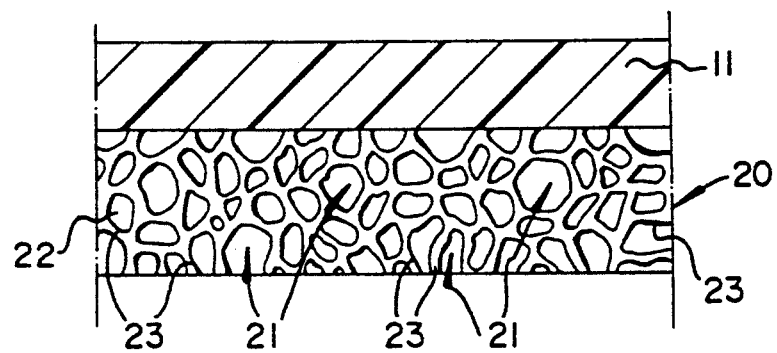
FIG. 12 is a sectional view of a conventional wound dressing.

For this purpose as well, with equine plasma collected in place of the equine serum 60 using the device in FIG. 9, the flow rate of it was measured in the same manner. FIG. 10 show the results.

These results also reveal that the plasma permeability of Types 2 and 3 (no test conducted with Type 3) is good.

(5) Animal experiment

Using a rabbit with a weight of about 3 kg, its dorsal region was shaved off and disinfected under general anesthesia with sodium pentobarbital, and a split-thickness skin defect having a depth of 20/1000 inch and a size of 25×50 mm was created with an electric dermatome. The wound surface was covered with each wound dressing, on which sterilized gauze and sterilized cut cotton were in turn placed, and was then pressed and fixed with elastic bandage. On the tenth post-operative day, the wound site was macroscopically observed, and the section of the wound was then histologically observed by hematoxylin and eosin stain. When the samples of Type 1, 2 and 3, wound dressings, respectively, were used, the macroscopic observations revealed the completion of epithelialization in each of them. In the histological observations, these samples presented the penetration of exudate into the wound dressings, as well as healthy graduation and epithelialization on the wound surface. Comparative examples such as BIOBRANE ®-type biosynthetic skin consisting of knitted nylon fabric bonded to an ultrathin silicone membrane by U.S. Woodroof Laboratories Inc.

and OPSITE ®-type adhesive backed polyurethane dressing by U.K. Smith and Nephew Medical Limited, i.e., commercially available wound dressings, were tested in the same manner. As a result, macroscopic observations showed little epithelialization in either of these dressings, and in histological observations, no permeation of exudate into the wound dressings was revealed in either, coupled with little healing confirmed o the wound surface.

It will be evident that various modifications can be made to the described embodiments without departing from the scope of the present invention.

For example, the film structure or texture of a wound dressing in accordance with the present invention can be modified in various ways depending upon the size and distribution of the above-described film-like objects, the size and distribution of pores, etc. In addition, the material, composition and other aspects of the dressing are not required to be limited to those stated above. The type and amount of a solvent to be used and the location of nylon mesh may be altered, and core material may be formed with a material other than nylon mesh. Further, the nylon mesh can be omitted.

As shown in FIG. 11, in addition, minute perforations 10 to be formed in a wound dressing can also be varied into small round shape (FIG. 11 (A)), slit-like cut 10′ penetrating from surface to back as in FIG. 11 (B), cross-shaped cut 10′ shaped cut 10′ penetrating from surface to back as in FIG. 11 (C), X-shaped cut 10′ penetrating from surface to back as in FIG. 11 (D), and tiny pinhole-shaped through-holes 10′ as in FIG. 11 (E). Those minute perforations shown in FIG. 11 (B) to (E) produce no cut-off residue when cuts or holes are formed, and in those shown in FIG. 11 (C) and (D) the state of the wound surface inside the dressing can be visually examined when the intersection of cross or X letter is turned up with fingers.

In regard to the above described manufacturing methods, moreover, the above-mentioned time of cyclohexane addition may be altered in the manufacturing process of, for example, a Type 3 dressing and, as occasion demands, for example, it may be added upon preparation of the homogeneous gel or dispersion gel, respectively.

In accordance with the present invention, as described above, since pores are contained in a three-dimensional structure made by minute film-like links, the contact area between the exudate and blood from the wound surface and the material is enlarged, thus enabling the acceleration of coagulation and incrustation, as well as increasing the mechanic strength. Moreover, the release efficiency of any drug present in dispersion on the surface of the material can be raised, and the barrier effect can be increased without reducing the permeability of moisture and vapor, so that higher dressing effect can be obtained at the stage that crust has been formed.

I claim:

1. A dressing for a wound comprising a porous structure of continuous pores throughout the dressing made of minute filaments arranged in three dimensions, and filmy links, viewed at a magnification of about 35 to 350, connecting the filaments, the porous structure having pores defined by the filmy interconnections.

2. A dressing for a wound as defined in claim 1, wherein the pores are continuous in the porous structure and connected to other pores by the filmy links; the dressing further comprising a wound-facing surface, an opposing surface and a volume disposed therebetween; the pores of the wound-facing surface and of the volume, respectively, being greater in number and larger than the pores of the opposing surface.

3. A dressing for a wound as defined in claim 1, wherein the porous structure is made of poly-α-amino acid.

4. A dressing for a wound as defined in claim 1, further comprising an antimicrobial agent.

5. A dressing for a wound as defined in claim 2, wherein the pores for the wound-facing surface and of the volume have a diameter of about 20 to 500 μm, and the pores of the opposing surface have a diameter up to about 20 μm.

6. A dressing for a wound as defined in claim 5, wherein the dressing has a thickness of about 0.1 to 10 mm and the opposing surface has a thickness of about 0.5 to 5 μm.

7. A dressing for a wound as defined in claim 1, further comprising a mesh of reinforcing material embedded in the porous structure.

8. A dressing for a wound as defined in claim 7, wherein the reinforcing material forms a border to the dressing, the pores on the wound-facing surface are smaller than the pores of the opposing surface.

9. A dressing for a wound as defined in claim 1, further comprising a plurality of perforations in the dressing between the wound-facing surface and the opposing surface.

10. A dressing for a wound comprising a porous structure of continuous pores throughout the dressing made of minute filaments arranged in three dimensions, and filmy links, viewed at a magnification of about 35 to 350, connecting the filaments, the porous structure having pores defined by the filmy interconnections and a mesh of reinforcing material embedded in the porous structure.

* * * * *